Figure 1:
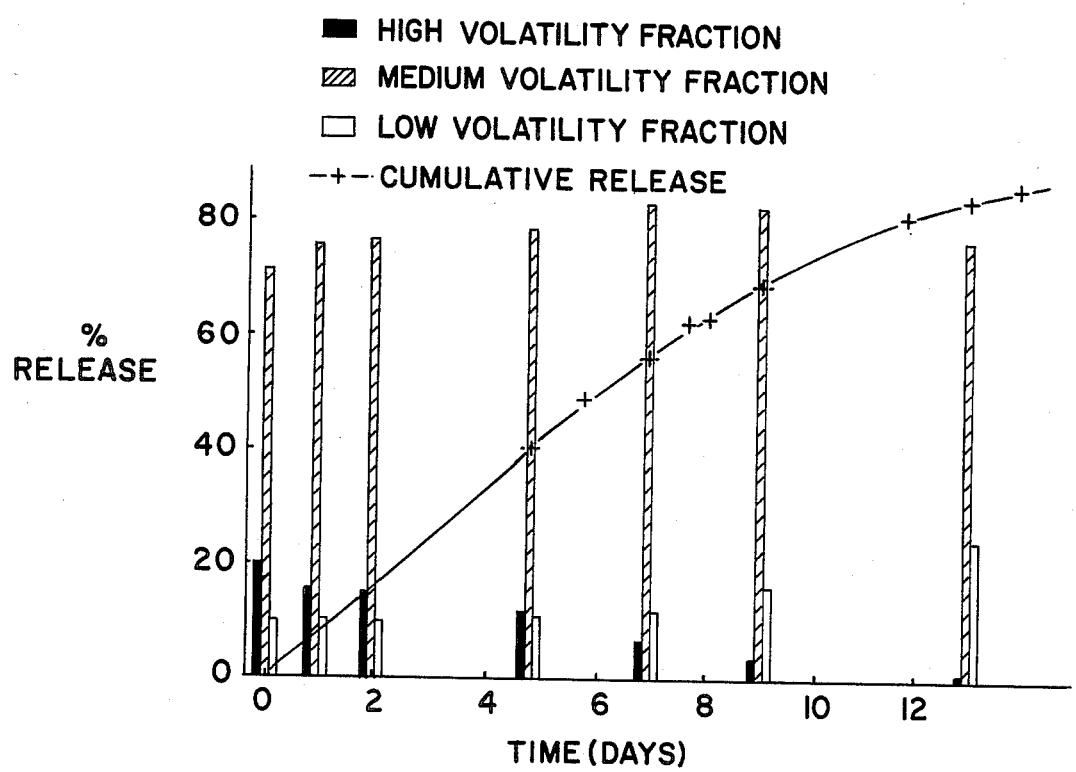

United States Patent [19]
Lee

[11] Patent Number: 4,729,190
[45] Date of Patent: Mar. 8, 1988

[54] MEMBRANE-FORMING POLYMERIC SYSTEMS

[75] Inventor: Ping I. Lee, Valley Cottage, N.Y.

[73] Assignee: Ciba-Geigy Corporation, Ardsley, N.Y.

[21] Appl. No.: 890,878

[22] Filed: Jul. 25, 1986

Related U.S. Application Data

[60] Division of Ser. No. 545,607, Oct. 27, 1983, abandoned, which is a continuation of Ser. No. 304,752, Sep. 23, 1981, abandoned.

[51] Int. Cl.$^4$ ................................................ A01C 1/06
[52] U.S. Cl. ................................... 47/57.6; 106/179; 106/176
[58] Field of Search ............................................ 47/57.6

[56] References Cited

U.S. PATENT DOCUMENTS

| | | | |
|---|---|---|---|
| 3,387,061 | 6/1968 | Smith et al. | 524/45 |
| 3,485,651 | 12/1969 | Ganz | 106/179 |
| 3,707,807 | 1/1973 | Graves | 47/576 |
| 3,758,433 | 9/1973 | Mullen | 524/375 |
| 3,968,310 | 7/1976 | Stowell | 428/411 |
| 3,969,280 | 7/1976 | Sayre et al. | 252/522 A |
| 4,221,601 | 9/1980 | Augustin | 106/197 C |
| 4,249,531 | 9/1981 | Heller | 128/260 |
| 4,256,505 | 3/1981 | Zweigle | 106/179 |
| 4,280,936 | 7/1981 | Dhabbar et al. | 106/197 C |

FOREIGN PATENT DOCUMENTS

| | | |
|---|---|---|
| 594495 | 3/1960 | Canada . |
| 651043 | 10/1962 | Canada . |
| 796370 | 10/1968 | Canada . |
| 911332 | 10/1972 | Canada . |
| 984084 | 2/1976 | Canada . |
| 1009144 | 4/1977 | Canada . |
| 1031260 | 5/1978 | Canada . |
| 1041788 | 11/1978 | Canada . |
| 1099429 | 4/1981 | Canada . |
| 1150964 | 8/1983 | Canada . |
| 2026517 | 2/1980 | United Kingdom . |

OTHER PUBLICATIONS

Chem. Abst. 84, 6195m (1976)–Saito et al.

*Primary Examiner*—Theodore Morris
*Attorney, Agent, or Firm*—Edward McC. Roberts; Harry Falber

[57] ABSTRACT

Membrane-forming polymeric systems comprising the molecular association product of a polymeric carboxylic acid having at least 10% of the monomer units containing free carboxylic groups with an ethoxylated nonionic surfactant; methods for the preparation of such polymeric systems; and a broad range of applications for such systems with particular emphasis on the release of diverse active agents at a continuous and controlled rate.

9 Claims, 4 Drawing Figures

MEMBRANE-FORMING POLYMERIC SYSTEMS

This application is a division of application Ser. No. 547,607, filed Oct. 27, 1983, which is a continuation of Ser. No. 304,752, filed on Sept. 23, 1981, both now abandoned.

Polymeric articles for the continuous dispensing of active agents into the environment of use are known. U.S. Pat. No. 3,567,118 discloses fabricated articles coated with a crosslinked hydrophilic polymer containing a volatile active agent. As a result of the cross-linking and thermosetting nature of the polymer, the coating has to be polymerized in situ under elevated temperatures in the presence of the volatile ingredient. One immediate shortcoming of this approach is that the high temperature experienced during such processing invariably results in a change of chemical properties of the volatile active agent, apart from any premature evaporation loss. In addition, the small solubility of volatile active agents in the polymer often limits the level of incorporated actives thereby restricting the duration of release from such articles. Similar drawbacks exist in systems disclosed in U.S. Pat. No. 3,705,938, i.e. nonporous polymer laminates, and in U.S. Pat. No. 3,975,350, i.e. crosslinked polyurethane hydrogels.

U.S. Pat. Nos. 3,578,545 and 3,985,298 utilize microporous polymeric materials for preparing impregnated and laminated plastic sheets containing volatile ingredients. However, the microporous sheet in these constructions must have sufficient porosity to permit a particular volatile active agent to pass through. Furthermore, the construction of laminates described the prior art frequently require cementing between polymer and substrate of dissimilar nature thereby increasing the processing difficulty and the frequency of delamination. Moreover, these prior art systems do not substantially minimize the undesirable fractionation among the components of a blended volatile active agent such as essential oils and pheromones. Fractionation is known to be undesirable since it reduces the efficacy and changes the quality of the volatile active ingredient. Thus, the pleasant fragrance that may initially be present will vary and disappear with the passage of time and with the resultant change in concentration of the various essential oil components. Correspondingly, the effective odor counteraction that may be achieved initially will also vary and diminish with time. Likewise, fractionation in pheromones may tend to impair the constancy of activity.

With respect to the disclosed polymer systems, the prior art describes either a crosslinked hydrophilic polymer system which has to be thermoset in situ, or a hydrophobic thermoplastic system which has to be hot melt extruded. None of the polymers described in the above prior art exhibit easily adjustable permeability and hydrophilicity/lipophilicity balance to accommodate the release of active agents of different nature hence unsatisfactory results are often obtained for the uses recited herein.

Further with regard to prior art systems, U.S. Pat. No. 3,387,061 discloses the chemical reaction product of a polycarboxylic acid and a polymeric polyether having an average molecular weight in excess of 4,000. The patent indicates that polyethers of the indicated molecular weight are essential in order to form a precipitate and, subsequently, to form coatings. It is to be noted, however, that such high molecular weight systems have limited permeability, reduced stability and reduced solubility in water and lower alcohols. Solubilization of active ingredient in such systems is frequently limited. Accordingly, the ability for such polymer systems to effectively control the rate and duration of release of active ingredients is negligible. It should also be noted that in addition to the high molecular weight limitation, the lack of surfactant nature in the components severely limits the achievable loading level and permeability of diverse active agents when such prior art reaction products are used in conjunction with the systems contemplated in the present invention.

Furthermore, Japan Kokai No. 7533,976 discloses the separation of nonionic detergents from dilute aqueous solutions by the addition of an aqueous solution of polycarboxylic acid. However, an excess of polycarboxylic acid solution and the presence of a water soluble salt with a polyvalent cation are required for the separation process. Moreover, the incomplete removal of nonionic detergent and the resultant presence of various impurities in the precipitate creates uncertainty as to the exact composition of the precipitate, a clearly disadvantageous situation. These prior art polymeric systems and their uses are therefore distinct from those of the present invention.

Accordingly, it is the primary object of the invention to provide molecular association polymer systems which are flexible and thermoplastic and which exhibit a wide range of permeabilities for varying active agents so as to be useful as membranes, coatings and carriers of various geometries, primarily for the controlled release of volatile and water-soluble active agents.

Another object of the invention is to provide a polymer system for the release of active agents at a controlled and uniform rate over a prolonged period of time, which system is relatively simple and economical to prepare.

Still a further object of the invention is to provide a polymer system which allows very high levels of active agent to be incorporated such that a more compact delivery system in the form of membranes, coatings and carriers of various geometries can be constructed.

Yet another object of the invention is to provide a delivery system which substantially minimizes fractionation among the components of mixed active agents such as essential oils and pheromones.

Still another object of the invention is to provide a polymer system which functions both as an adhesive layer as well as a rate controlling membrane for the release of active agents, when it is coated on or laminated to a substrate containing said active agents.

A further object is to identify a broad range of applications for said polymer systems.

Other objects and advantages of the invention will become apparent to those skilled in the art from the following detailed description of this invention taken in conjunction with the drawings and accompanying claims.

The foregoing objects of the invention are attained by the unexpected discovery that a blend of a polymeric carboxylic acid and an ethoxylated nonionic surfactant at a weight ratio ranging at least from 1:20 to 20:1, and preferably from 1:4 to 4:1, yields a rubbery and thermoplastic system having a low and adjustable glass transition temperature, and exhibiting flexibility in terms of permeabilities for various active agents. The polymeric carboxylic acids employed herein include those acidic polymeric materials in which the acidity is due to free carboxylic acid groups with a minimum of about 10% of the monomer units comprising carboxylic groups. The ethoxylated nonionic surfactants suitable for the purpose of the invention contain a minimum of 2 ethylene oxide units, have HLB (hydrophile-ilophile balance) values between 2 and 40 and have molecular weights ranging up to about 4,000. These compatible blends, which can be readily prepared at room temperature, are totally amorphous and distinctly different from the parent components with respect to their physical state, flexibility, glass transition temperatures, and permeabilities to a diversity of volatile and water-soluble active agents. The amorphous structure and the low glass transition temperature make it an ideal membrane material for the controlled release of active ingredients.

The present polymer system is unique over those of the prior art inasmuch as an adjustment in the ratio and type of polymeric carboxylic acid and ethoxylated nonionic surfactant components permits the practitioner to prepare polymers with extremely wide ranges of application possibilities, particularly with regard to permeabilities to various volatile and water-soluble active agents. The polymer systems of this invention are therefore particularly suitable as membranes, coatings, granules and other type of carriers for the controlled release of active agents over a prolonged period of time via a diffusion mechanism. Depending upon the particular environment in which the polymer system is used, applicable volatile active agents may be essential oil, medicament, pheromone, anti-microbial, anti-bacterial, anti-fungal, insecticidal, herbicidal, and other volatiles. The polymer system is equally applicable as a control release membrane for active ingredients which exhibit a minimum water solubility. The exact degree of water solubility will vary widely depending on the release requirements. Accordingly, for purposes of this invention, the term "active agent" is intended to include both volatile and water-soluble materials. The polymers are also applicable as protective coatings for a wide variety of substrates, as adhesives, and the like.

The incorporation of an ethoxylated nonionic surfactant as one of the components in the present invention is particularly advantageous in that the solubilization power of the surfactant enables a higher than usual level of active agent to be loaded into the polymer when it is used directly as an active agent carrier. Up to 50% or more loading can easily be achieved by first solubilizing the active agent in a nonionic surfactant in liquid state prior to the blending with polymeric carboxylic acid. This capability avoids the drawback of low active loading levels generally associated with the prior art systems.

Another advantage of the invention is that the polymer system and controlled release articles containing active agents made therefrom can readily be formed at room temperature, about 20°-25° C., via mixing, coating or extrusion processes known to those skilled in the art. This capability obviates the decomposition and/or premature volatization of volatile active agents experienced in the prior art when processing under elevated temperatures. Moreover, when the polymer is coated on or laminated to a substrate containing an active agent, it uniquely serves a dual function as an adhesive and as a rate controlling membrane for the release of active agent into the intended environment. A further important advantage of the instant system is the ability to minimize undesirable fractionation among the components of a mixture type of volatile active agent such as essential oils and pheromones. As a result, there is a uniformity in composition and potency of the volatile active agent throughout the entire period of activity of the controlled release system.

Accordingly, the present invention relates to polymeric systems and articles made therefrom, said systems comprising a blend of a polymeric carboxylic acid and an ethoxylated nonionic surfactant at a weight ratio ranging from at least 1:20 to 20:1, and preferably from 1:4 to 4:1.

The polymeric carboxylic acid which may be employed in accordance with this invention may generally be described as an acidic polymeric material in which the acidity is provided by free carboxyl groups. Such polymeric materials and methods for their preparation are well known in the art. Included among such acidic materials are synthetic polymers as well as natural polymers such as alginic acid, pectic acid and cellulose glycolic acid. An illustrative but by no means exhaustive listing of suitable polymeric carboxylic acid components include homopolymers of unsaturated carboxylic acids such as acrylic acid, methacrylic acid, and the like; copolymers of monocarboxylic acids of the acrylic series with one or more polymerizable vinyl or vinylidene compounds such as vinyl halides, vinyl acetate, vinyl benzoate, acrylonitrile, methacrolein, styrene, vinyl toluene, methyl methacrylate, ethyl acrylate, vinyl methyl ketone, vinyl methyl ether, t-butylacrylamide, N-dimethylacrylamide, and the like; or hydrolyzed copolymers of alpha, beta-ethylenically unsaturated dicarboxylic acid anhydrides, e.g. maleic anhydride with one or more terminally unsaturated monoolefins such as ethylene, propylene, isobutylene, diisobutylene, chloroprene, and the like; or with cyclic terpenes such as dipentene; or with vinyl or vinylidene compounds such as vinyl halides, vinyl esters, vinyl others, vinyl ketones, styrene, acrylic acid and its esters, methacrylic acid and its esters, and the like. Detailed descriptions of polymerizable vinyl, vinylidene and related compounds and the preparation of their copolymers known to the art are discussed in *Vinyl and Related Polymers* by Calvin E. Schildknecht, 1952, published by John Wiley & Sons, Inc.

It will be understood that the polymeric carboxylic acid which may be employed in accordance with this invention may also be prepared by carboxyalkylation of polymers containing a multiplicity of hydroxyl groups such as polyvinyl alcohol, partially hydrolyzed polyvinyl acetate, cellulose and its derivatives, dextran and its derivatives, and the like; and by hydrolysis of polymers containing a multiplicity of acrylamide or acrylonitrile groups such as polyacrylamide, polyacrylonitrile, and the like in the presence of an alkaline catalyst. Carboxyalkylation of hydroxyl groups can be accomplished by methods well known to the art such as by reaction with chloroacetic acid in the presence of alkali, or by reactions with acid anhydrides derived from dicarboxylic acids such as phthalic anhydride, maleic anhydride, succinic anhydride, and the like to form half esters. Furthermore, the derivatives of any of the aforementioned polymers wherein a fraction of the carboxylic acid groups are reacted to form derivatives thereof such as partial amide by treatment with ammonia and organic amines, and partial esters by treatment with lower alkyl alcohols may also be used. It is essential, however, that a minimum of 10% carboxylic acid groups be retained in the latter derivatives. In addition, the monomers and the resulting polycarboxylic acid in accordance with this invention may likewise be substituted by one or more other groups such as, halide, hydroxy, ester, ether, alkyl, aryl, phenoxy, alkylphenoxy, dialkylamino, perfluoroalkyl, perfluoroalkoxyperfluoroalkyl, polysilanyl-alkyl, thiol and the like. Other polymeric carboxylic acids in accordance with the invention may include a polycarboxylic acid ether having aliphatic chains alternating with and connected by ether oxygen to residues of a pentanoic acid as described in U.S. Pat. No. 3,300,444, and a carboxy polymethylene hydrocolloid based on the acrylic and methacrylic acid form of polymer containing 0.75 to 2% by weight of polyalkenyl polyether as a crosslinking agent as disclosed specifically in U.S. Pat. No. 2,909,462. As previously noted, the overall composition of the polycarboxylic acid component is not critical, provided that at least 10% of the monomer units contain free carboxylic acid groups.

Preferred polymeric carboxylic acid components include polyacrylic acid, polyacrylic acid crosslinked with approximately 1% of polyallyl sucrose, polymethacrylic acid, polymaleic acid, polyitaconic acid, polyhydroxybenzoic acid, polygalacturonic acid, polyglutamic acid, polyglycollic acid, polylactic acid, ethylene/acrylic acid copolymer, ethylene/methacrylic acid copolymer, methylmethacrylate/methacrylic acid copolymer, methyl acrylate/methyl methacrylate/methacrylic acid terpolymer, ethyl acrylate/t-butyl acrylamid/acrylic acid terpolymer, methyl vinyl ether/maleic acid copolymer, vinyl acetate/crotonic acid copolymer, butadiene/maleic acid copolymer, polymaleic anhydride, acrylonitrile/maleic anhydride copolymer, butadiene/maleic anhydride copolymer, ethylene/maleic anhydride copolymer, 1-hexene/-maleic anhydride copolymer, 1-octadecene/ maleic anhydride copolymer, methyl vinyl ether/maleic anhydride copolymer, n-octadecyl vinyl ether/maleic anhydride copolymer, styrene/maleic anhydride copolymer, vinyl acetate/maleic anhydride copolymer, cellulose acetate phthalate, carboxymethyl cellulose and carboxyl modified polyacrylamide.

Within the preferred embodiment of this invention the polymeric carboxylic acid should have a minimum of 10%, and preferably above 20%, and still more preferably above 50% of the monomer units comprising carboxylic acid groups. In general, the average molecular weight of the polymeric carboxylic acid to be employed may range from about 1,500 up to 4,000,000 and higher.

The ethoxylated nonionic surfactants contemplated for use in the systems of this invention include ethoxylated alkylphenols, ethoxylated mono- and polyhydroxy aliphatic alcohols, ethoxylated fatty amines, ethoxylated fatty acid amides and ethanolamides, ethoxylated fatty acids, ethoxylated fatty acid esters, ethoxylated sorbitan fatty acid esters, ethoxylated sorbitol esters, ethoxylated vegetable oils, ethoxylated lanolin derivatives, ethoxylated sugar derivatives, ethoxylated naphthalene derivatives, ethoxylated mercaptans, ethoxylated polypropylene glycols, ethoxylated fatty glycerides, ethoxylated fatty glycol esters, ethoxylated sucroglycerides, and the like. The applicable ethoxylated nonionic surfactants may be primary, secondary, tertiary, saturated, unsaturated, linear or branched in structure. The backbone and pendant chain of the said surfactants may be substituted in part by one or more other groups such as halide, hydroxyl, ester, ether, alkyl, aryl, phenoxy, alkylphenoxy, dialkylamino, perfluoroalkyl, perfluoroalkoxyalkyl, silicone, silane, thiol and the like, e.g. the compositions disclosed in U.S. Pat. Nos. 2,915,554 and 4,171,282. Other ethoxylated nonionic surfactants applicable herein include perfluoroalkyl polyurethane surfactants as disclosed in U.S. Pat. No. 4,046,944. The foregoing illustrative listing of applicable ethoxylated nonionic surfactants is by no means exhaustive of the surfactants which can be used, it being required of applicable surfactants that the ethylene oxide content be sufficiently large to enable them to behave in the manner of a nonionic surfactant. Detailed descriptions of ethoxylated nonionic surfactants and processes for their preparation known to the art are discussed in *Nonionic Surfactants*, edited by M. J. Schick, 1970, published by Marcel Dekker, Inc., and in *Surfactants* and *Interfacial Phenomena* by M. J. Rosen, 1978, published by John Wiley & Sons, Inc., such teachings being incorporated by reference herein.

Preferred surfactants include octylphenoxy polyethoxy ethanols, nonylphenoxy polyethoxy ethanols, exthoxylated sorbitan monolaurates, ethoxylated sorbitan monopalmitates, ethoxylated sorbitan monostearates, ethoxylated sorbitan monooleates, ethoxylated sorbitan tristearates, ethoxylated sorbitan trioleates, ethoxylated oleyl amides, ethoxylated tallow amides, ethoxylated glycol laurates, ethoxylated glycol stearates, ethoxylated glycol oleates, ethoxylated stearic acid, ethoxylated oleic acid, ethoxylated rosin fatty acids, ethoxylated lauryl ethers, ethoxylated cetyl ethers, ethoxylated stearyl ethers, ethoxylated oleyl ethers, ethoxylated tridecyl ethers, ethoxylated polydimethylsiloxanes, ethoxylated polypropylene glycols, ethoxylated polyurethanes, and ethoxylated perfluoroalkyl polyurethanes.

Within the preferred embodiment of this invention, the ethoxylated nonionic surfactants contemplated should comprise a minimum of 2 and preferably at least 5 ethylene oxide units and have HLB (hydrophile-lipophile balance) values between 2 and 40 and preferably between 4 and 18. The HLB system identifies the lipophilic and hydrophilic character of surfactants and is fully described in a bulletin distributed by ICI Americas Inc. Surfactants with HLB values less than 10 are generally insoluble in water, while those with HLB values greater than 10 are generally water soluble. In general, the average molecular weight of the ethoxylated nonionic surfactant to be employed may range from about 150 to 4,000 and preferably up to 3,500.

The process of forcing a homogeneous blend, in accordance with the present invention, involves blending the indicated polymeric carboxylic acid and ethoxylated nonionic surfactant under conditions and subsequent treatment as explained hereinafter as determined by the end use requirements of the systems. Thus, since most of the blends so formed are relatively insoluble in water, it is preferred to dissolve the polymeric carboxylic acid and ethoxylated nonionic surfactant in separate solvents or water-solvent mixtures (which can be the same solvent or different but miscible solvents) in the desired concentration, and subsequently to add one solution to the other such that a solution of the blend is formed from which useful membranes, coatings and other finished forms such as carriers for the controlled release of active agents can be prepared. The solution of the said blend can also be prepared by dispersing the polymeric carboxylic acid in a nonsolvent or solvent-nonsolvent mixture, followed by mixing the resulting dispersion with a miscible or soluble ethoxylated nonionic surfactant. Depending upon the nature of the components in the blend, the applicable solvents and nonsolvents contemplated include alcohols such as methanol, ethanol, isopropanol, and the like; alkylene glycols such as ethylene glycol, propylene glycol, and the like; monoalkyl ethers of alkylene glycols such as monomethyl ether of ethylene glycol, and the like; aliphatic and aromatic hydrocarbons such as hexane, toluene, and the like; halogen substituted aliphatic and aromatic hydrocarbons such as methylene chloride, carbon tetrachloride, chlorobenzene, and the like; ketones such as acetone, methyl ethyl ketone, and the like; esters such as ethyl acetate, butylacetate, and the like; and water, dioxane, formamide, dimethyl formamide, dimethyl sulfoxide, and the like. When a water-solvent or solvent-nonsolvent mixture is involved, the amount of solvent employed should be at least sufficient to prevent precipitation of the blend. Generally, at least about 20%, based on the total mixture weight, of solvent is required.

Within the preferred embodiment of this invention the homogeneous blend of a polymeric carboxylic acid, with a minimum of 10%, and preferably above 20%, and still more preferably 50% of the monomer units comprising carboxylic groups, and a nonionic surfactant, with a minimum of 2 and preferably at least 5 ethylene oxide units and with HLB values between 2 and 40 and preferably between 4 and 18, should have a component weight ratio ranging at least from 1:20 to 20:1 and preferably from 1:4 to 4:1 and most preferably an optimum range from 2:3 to 3:2. The optimum solids content in the solution of said blend is readily determined by routine experimentation according to the viscosity requirements in the intended fabrication process, such as coating or extrusion. The temperature at which the polymer blend is formed can range from 10° C. to 130° C. and is preferably at an ambient or room temperature of about 20°-25° C. The blend so formed, after evaporating the solvent by air-drying or under reduced pressure, is generally homogeneous, totally amorphous, thermoplastic, rubbery, and distinctly different from the parent components with respect to physical state flexibility, glass transition temperature, and permeability to active agents. In every instance, the homogeneous blend of a brittle, solid polymeric carboxylic acid and a liquid or paste ethoxylated nonionic surfactant results in a rubbery, thermoplastic polymer having a low and adjustable glass transition temperature which exhibits adjustable permeabilities for various active agents. The extent of change in properties of the blend from those of the starting components can not be accounted for from simple mixing alone. Without wishing to be bound by a theory of operation, the probable mechanism by which the variation in property is achieved is through an intermolecular complex formation between the polymeric carboxylic acid and the ethoxylated nonionic surfactant in the solid phase. This is manifested by the observation that when an ethoxylated nonionic surfactant is blended with the aqueous solution of the polymeric carboxylic acid, an immediate increase in viscosity is observed which eventually results in the gelation of the mixture.

The polymer blends of this invention are generally soluble in an alkaline metal hydroxide solution with pH above about 4.5. However, upon drying the said solution by air or under reduced pressure, a phase separation between the polymeric carboxylic acid salt and the ethoxylated nonionic surfactant would result if the polymeric carboxylic acid is neutralized to the extent that less than about 10% of the monomer units comprise free carboxylic acid groups. Thus, the presence of free carboxylic acid groups is essential in the association of a polymeric carboxylic acid and an ethoxylated nonionic surfactant in the solid state. As previously noted, the overall composition of the polymeric carboxylic acid component is not critical to the formation of polymeric blends providing it contains a minimum of 10%, preferably above 20%, and still more preferably at least 50% of the monomer units as carboxylic acid groups.

The polymer system of the present invention is not limited to blends of a single polymeric carboxylic acid and a single ethoxylated nonionic surfactant. In fact, one or more polymeric carboxylic acids and one or more ethoxylated nonionic surfactants within the preferred embodiment of this invention can be utilized to form the blend. In addition, other compatible additives such as dyestuffs, pigments, plasticizers, UV-stabilizers, inorganic fillers including amorphous silica, bentonite and the like, and water soluble synthetic and natural polymers including polyvinyl alcohol, methyl cellulose, carboxymethyl cellulose, sodium alginate, carrageenan, and the like can be used in forming the polymer system of the present invention to improve the appearance, stability, solvent resistance, and mechanical properties of the resulting articles.

The present invention is unique over prior art systems in a view of its adaptability to adjustment of the ratio and type of polymeric carboxylic acid and ethoxylated nonionic surfactant components to prepare polymers with an extremely wide spectrum of performance characteristics such as permeability to various active agents. The blends provided in this invention are therefore particularly suitable as membranes, coatings, granules and other type of carriers, with particular emphasis on the controlled release of volatile and water-soluble active agents into the environment of use over a prolonged period of time. The mechanisms of controlled release involves the dissolution of the active agent in the polymer phase, diffusion through the polymer and then desorption of ingredient from the external polymer surface into the environment of use.

The expression "volatile active agent" as used herein broadly includes any compound, composition of matter or mixture thereof with measurable vapor pressure at the temperature of intended usage, that can be delivered from the system of instant invention. Depending upon the particular environment of use in which the system of instant invention is used, the applicable volatile and/or water soluble active agents may include essential oils, pheromones, medicaments, germicides, algicides, biocides, fungicides, disinfectants, insecticides, pesticides, herbicides, and other volatiles. The term "essential oils" includes perfumes and other conventional volatile odorous air-treating agents. The term "pheromones" generally includes insect sex attractants and repellents. The term "medicaments" includes physiologically or pharmacologically active substances that produce a localized or systemic effect in humans and other animals. The active medicaments that can be delivered into the environment of use include bronchodilators, vascodilators, inhalational expectorants, and the like. The phrase "environment of use" as used herein refers to the atmosphere surrounding an active agent-releasing system including surfaces within its vicinity such as nasal receptors, respiratory tracts, skin, bark, soil, leaves, roots, insects, cytoplasmic membranes, and the like where the said volatile active agent can be deposited from vapor state or where said water-soluble active agent can be deposited in the liquid state.

The criteria for selecting an optimum component ratio of polymeric carboxylic acid and ethoxylated nonionic surfactant within the prescribed range, will vary according to the intended area of utility. However, a practitioner can readily ascertain the optimum ratio of components by testing the permeation and release properties of the resulting blend. This is achieved by following the weight loss of a active agent from an article prepared from the said blend as a function of time.

Another embodiment of the instant invention is directed to the method of preparation of articles containing the blend described herein for the controlled release of active agents into the environment of use over a prolonged period of time. Thus, a viscous solution of the said blend can be coated directly onto an absorbent substrate by conventional means such as dip-coating, doctor blades, wire-wound rods, roller mills, gravure rolls, and the like, followed by air drying or drying under reduced pressure. The absorbent substrate in the form of sheet, pad, granule, cylinder or other convenient shape may be either a woven or nonwoven material including cloth, felt, paper and the like, comprising cellulosic fibers, cellulose ester fibers, crosslinked polyvinyl alcohol fibers, polyvinyl chloride fibers, acrylonitrile fibers, glass fibers, nylon fibers, polyethylene terephthalate fibers, wools, silks, and the like. Alternatively, foamed polymeric material such as open pore polyurethane foam and the like can also be utilized.

The said absorbent substrate can then be impregnated with a volatile active agent either prior to or after the coating process but preferably the latter. Optionally, after the impregnation of the coated substrate with a volatile active agent, the uncoated side of the substrate can be coated with a viscous solution of the blend and laminated either to a barrier backing material impermeable to the said volatile active agent such as aluminum foil, high density polyethylene film, polyvinylidene chloride film, polyacrylonitrile film and the like, or to the uncoated side of similarly prepared impregnated substrates to form a sandwich structure. The articles so formed contain a volatile active agent reservoir enclosed with a release rate-controlling membrane and therefore provide a prolonged and controlled release of the said volatile active agent into the environment of use via a solution-diffusion mechanism.

With respect to the direct coating onto an absorbent substrate, the viscosity of the solution of the polymer blend described herein is generally increased by adjusting the solids content to an extent such that it is flowable and castable yet still viscous enough to prevent any appreciable penetration into the absorbent, porous substrate. Consequently, any adverse effect on the rate controlling property of the coated membrane layer is avoided. Alternatively, and preferably, a thin sheet of woven or nonwoven material of lesser porosity than the absorbent substrate but still freely permeable to various volatile active agents can be coated with a viscous solution of the blend described herein to form a supported, penetration free membrane. Before being completely dry, the said membrane coated sheet exhibits slight tack and thus can be laminated to the absorbent substrate described previously. The thin sheet of woven or nonwoven material employed herein can also be decorated or printed to provide an attractive appearance. Still another manner of fabricating the said coated article is by casting the coating solution of the blend onto a release liner such as silicone treated release paper, Teflon film and the like to form a penetration free membrane. After evaporating the solvent by air-drying or under reduced pressure, the membrane is thermally or mechanically transferred from the release liner onto the previously described absorbent substrate under an applied pressure of, for example, 1 to 50 psi at a temperature of 50° to 130° C.

An important advantage of the said membrane coated or laminated articles for the controlled release of volatile active agents is their unexpected property of minimizing fractionation among the components of a mixture type of volatile active agent such as essential oils and pheromones. Thus, contrary to prior art systems which exhibit fast release of the low boiling components followed by release of the components boiling at medium and high temperature ranges, the instant systems exhibit similar percentage releases for all three portions through the rate controlling membrane. As a result, there is uniformity in composition and potency of volatile active agent throughout the entire period of activity of the controlled release system.

Another method for forming the blend of the instant invention and controlled release articles containing active agents made therefrom involves solubilizing a active agent directly in an ethoxylated nonionic surfactant in liquid state prior to the blending with a liquid or powdery polymeric carboxylic acid without any solvent. The incorporation of an ethoxylated nonionic surfactant as one of the components in the present invention is particularly advantageous in that the solubilization power of the surfactant enables a higher than normal level, up to 50% or more, of active agents to be incorporated into the polymer when it is used directly as an active agent carrier. This high level of active agent loading would have been thought to be impossible to achieve in prior art systems due to phase separation.

The active agent-containing blend so formed has the consistency of a plastic dough. By changing the nature and fraction of the ethoxylated nonionic surfactant in the blend or by dissolving the ethoxylated nonionic surfactant in a small amount of solvent prior to the formation of the blend, the plasticity of the blend can be adjusted to suit a desired fabrication process. Thus, the active agent-containing blend so prepared may be molded or extruded to form shaped articles, sheets, cylinders, granules and the like at ambient or room temperature, about 20°-25° C. They may also be foamed or blown by techniques known to those skilled in the art for paste or organosol compositions and may further be mixed with inert fillers, dyes, pigments, and the like. Alternatively, the blend may be dissolved in a suitable solvent and then used as a coating for granulated materials, woven and nonwoven materials, paper, wood, metal and plastic surfaces, and surfaces of other shaped articles for the controlled release of incorporated active agents into the environment of use over a prolonged period of time.

The unique polymer systems are also available for use in a broad range of applications unrelated to the controlled release of volatile active ingredients. Thus, they can be used as coatings for solid, non-volatile active ingredients to provide controlled release thereof. For example, they can function as coatings for pharmaceutical tablets to provide controlled release in-vivo in humans and animals. They can provide comparable controlled release of herbicides and insecticides. They can be used strictly as protective coatings for a wide variety of substrates, providing both water and oil repellancy. In the latter area, they can function as bandage-type materials to protect skin abrasions and other wounds. The systems can be formed into pouches for release of a wide variety of materials, including delivery of medications to the skin or mucosa. As previously noted, incomplete drying of the films will provide a residual tackiness, enabling the systems to be utilized as adhesives with excellent tear and peel strengths. Finally, the systems can be utilized as seed coatings to provide greater control of the germination process without adversely effecting the total percentage of seed germination. Such coatings can also function to adjust the size of the seed where such adjustment is desirable. Correspondingly, fungicides, safeners, and the like, can be incorporated in the polymeric systems for controlled release during the entire germination cycle.

The following examples will further illustrate the embodiments of the present invention. In these examples, all parts and percentages given are by weight unless otherwise noted.

Examples 1-14 deal with the preparation of various polymer blends of the present invention and identification of their associated physical characteristics utilizing test methods such as X-ray diffraction, differential scanning calorimetry, tensile measurement and the like.

EXAMPLE 1

A blend was prepared utilizing 25 parts of octylphenoxy polyethoxy ethanol having 9–10 ethylene oxide units, an HLB value of 13.5 and an average molecular weight of 628, and 125 parts of 20% aqueous solution of polyacrylic acid having an average molecular weight of 250,000. An immediate increase in viscosity followed by precipitation was observed upon mixing. After air drying at room temperature, a clear, rubbery, thermoplastic polymer having a polyacrylic acid to octylphenoxy polyethoxy ethanol ratio of 1 to 1 suitable for use in the instant invention to provide prolonged and controlled release of volatile active agent was obtained. This polymer was determined to be totally amorphous having a low glass transition temperature Tg of $-15.5°$ C. and a tensile strength of 283 psi at 25° C.

EXAMPLE 2

The procedure of Example 1 was repeated using 12.5 parts of said octylphenoxy polyethoxy ethanol and 187.5 parts of said 20% aqueous solution of polyacrylic acid. After air drying at room temperature, a clear, highly flexible, thermoplastic polymer having a polyacrylic acid to octylphenoxy polyethoxy ethanol ratio of 3 to 1 was obtained. This polymer was less flexible than the product of Example 1 and was determined to be totally amorphous having a glass transition temperature Tg of $-2°$ C. and a tensile strength of 560 psi a 25° C.

EXAMPLE 3

The procedure of Example 1 was repeated using 37.5 parts of said octylphenoxy polyethoxy ethanol and 62.5 parts of said 20% aqueous solution of polyacrylic acid. After air drying at room temperature, a clear, rubbery, thermoplastic polymer having a polyacrylic acid to octylphenoxy polyethoxy ethanol ratio of 1 to 3 was obtained. This polymer was more flexible than the product of Example 1 and was determined to be totally amorphous having a glass transition temperature of $-35.5°$ C.

EXAMPLE 4

A 20% aqueous solution of ethylene-maleic acid copolymer was prepared from EMA-31, an ethylene-maleic anhydride resin with an average molecular weight of 100,000 manufactured by Monsanto. Thereafter, 25 parts of the solution were blended with 10 parts of 50% aqueous solution of a nonionic surfactant PEG 1540 monostearate (polyethylene glycol stearate ester with average molecular weight about 1,800 and HLB value of 17.3, manufactured by Armak Co.) to form a 1 to 1 blend. An immediate increase in viscosity was observed upon mixing. After drying overnight at 40° C., the product was clear, flexible and insoluble in water, lower alcohols and dimethylformamide (DMF) in contrast to the brittleness and good water, alcohol and DMF solubility of EMA-31 solid as shown in Table 1.

EXAMPLE 5

Example 4 was repeated except that PEG 1540 monooleate (average molecular weight of 1,800 and HLB value of 17.0) was used instead of PEG 1540 monostearate. After drying overnight at 40° C., the resulting product was also clear, flexible and insoluble in water, lower alcohols and DMF as shown in Table 1.

EXAMPLE 6

Approximately 5 parts of styrene-maleic anhydride resin (average molecular weight of 50,000, manufactured by Scientific Polymer Products, Inc.) was dissolved in 25 parts of acetone to form a solution with a solids content of 16.67%. The solution was then mixed with 10 parts of a 50% aqueous solution of PEG 1540 monooleate to form a 1 to 1 blend. An immediate increase in viscosity was observed upon mixing. After drying overnight at 40° C., the product was clear, moldable and insoluble in lower alcohols, acetone and DMF in comparison with the brittleness and good alcohol, acetone and DMF solubility of styrene maleic anhydride resin as shown in Table 1.

EXAMPLE 7

Example 6 was repeated except that Ethomid HT/60 (ethoxylated fatty acid amide with average molecular weight of 2,478 and 50 ethylene oxide units, manufactured by Armak Co.) was used instead of PEG 1540 monooleate. After drying overnight at 40° C., the resulting product was clear, flexible and insoluble in lower alcohols, acetone and DMF as shown in Table 1.

TABLE 1

| | Solubility Characteristics of Association Polymers at 25° C. | | | | | | |
|---|---|---|---|---|---|---|---|
| Description | Composition | Water | Ethanol | Methanol | Acetone | DMF | Description |
| Ethylene Maleic Anhydride Copolymer (EMA) | 100% | S | S | S | I | S | y,b |
| EMA/PEG 1540 Monostearate (Ex. 4) | 1:1 | I | I | I | I | I | c,f |
| EMA/PEG 1540 Monooleate (Ex. 5) | 1:1 | I | I | I | I | I | c,f |
| Styrene Maleic Anhydride Copolymer (SMA) | 100% | I | S | S | S | S | c,b |
| SMA/Ethomid HT/60 (Ex. 7) | 1:1 | I | I | I | I | I | y,t,f |
| SMA/PEG 1540 Monooleate (Ex. 6) | 1:1 | I | I | I | I | I | c,m |

TABLE 1-continued

| | | | | | | | |
|---|---|---|---|---|---|---|---|
| SMA/Tween 80 (Ex. 8) | 1:1 | I | I | I | I | I | y,t,f |

Key

Solubility: S = Soluble
I = Insoluble

Description: b = brittle
c = clear
f = flexible
m = moldable
t = transparent
y = yellow

EXAMPLE 8

Example 6 was repeated except that an ethoxylated sorbitan monooleate having 20 ethylene oxide units, an HLB value of 15 and an average molecular weight about 1,300 (Tween 80 by ICI Corp.) was used instead of PEG 1540 monooleate. After drying overnight at 40° C., the resulting product was also clear, flexible and insoluble in lower alochols, acetone and DMF as shown in Table 1.

EXAMPLE 9

Approximately 15 parts of cellulose acetate phthalate containing 19–23.5% acetyl groups and 30–36% of phthalyl groups was dissolved in 85 parts of a mixture of 249 parts anhydrous acetone and 1 part of water to form a solution having a viscosity range of 50–90 centipoises at 25° C. The solution was then blended with 22.5 parts of Tween 80 and an immediate increase in viscosity was observed.

The solution so formed was knife cast onto a glass plate. After air drying at room temperature, a clear, flexible, thermoplastic and slightly elastic film having a polymeric carboxylic acid to ethoxylated nonionic surfactant ratio of 2 to 3 was obtained which was suitable for use in the instant invention to provide prolonged and controlled release of active agents.

EXAMPLE 10

Approximately 2 parts of PA-6 (a linear copolymer of 1-hexene and maleic anhydride with average molecular weight about 50,000, manufactured by Gulf Oil Co.) was dissolved in 18 parts of ethanol to form a solution of 10% solids content. Approximately 2 parts of this solution were mixed with 0.2 parts of Triton N-111 (nonylphenoxy polyethoxy ethanol having 11 ethylene oxide units, HLB value of 13.8 and an average molecular weight of 704, manufactured by Rohm and Haas Co.) to form a 1 to 1 blend. An immediate increase in viscosity was observed. After drying at 40° C. for 2 hours, a clear, elastic film suitable for use in the instant invention to provide prolonged and controlled release of active agents was obtained.

EXAMPLE 11

Example 10 was repeated except that Tween 80 was substituted for Triton N-111. After drying at 40° C. for 2 hours, a clear, elastic film was formed as compared with the brittle solid formed from PA-6 alone.

EXAMPLE 12

Five parts of 50% ethanol solution of a 40:40:20 mole % ethyl acrylate, t-butyl acrylamide and acrylic acid terpolymer having about 20% carboxylic acid content and an average molecular weight of 35,000 was mixed with 2.5 parts of Triton N-101 (nonylphenoxy polyethoxy ethanol, having 9–10 ethylene oxide units, HLB value of 13.4 and an average molecular weight of 642, manufactured by Rohm and Haas Co.) to form a 1 to 1 blend. An immediate increase in viscosity was noticed. Upon drying at 40° C. for 2 hours, an elastic, clear film product was obtained.

EXAMPLE 13

One part of Triton N-101 was blended with 20 parts of a 2.5% aqueous solution of polymethacrylic acid having an average molecular weight of about 200,000. Immediate precipitation was observed upon mixing. After air drying at room temperature, a clear, rubbery, thermoplastic polymer having a polymethacrylic acid to Triton N-101 ratio of 1 to 2 was obtained which was suitable for use in the instant invention to provide prolonged and controlled release of active agents.

EXAMPLE 14

Example 13 was repeated except that Tween 80 was substituted for Triton N-101. Immediate precipitation was observed upon mixing. After air drying at room temperature, a clear, rubbery, thermoplastic polymer having a polymethacrylic acid to Tween 80 ratio of 1 to 2 was obtained which was suitable for use in the instant invention to provide prolonged and controlled release of active agents.

EXAMPLE 15

This example illustrates a typical method of preparation of controlled release articles using the polymer systems of the present invention as well as the advantages obtained from such systems.

25 parts of octylphenoxy polyethoxy ethanol having 9–10 ethylene oxide units, an HLB value of 13.5 and an average molecular weight of 628, were blended with 125 parts of 20% water/isopropanol (3 to 1 weight ratio) solution of polyacrylic acid having an average molecular weight of 250,000. The presence of isopropanol as a cosolvent prevented the precipitation of the blend. The resulting solution of the blend had a polyacrylic acid to octylphenoxy polyethoxy ethanol ratio of 1 to 1, a solids content of 33.3% and a Brookfield viscosity of 10,000 cps at 25° C.

The solution so formed was knife coated with a 10 mil wet laydown onto one surface of a 45 mil blotter paper (210 lb. basis weight). Immediately after the casting, the coated blotter was air dried at 50° C. The uncoated side of the absorbent blotter was then impregnated with approximately 0.08 lb/ft$^2$ of citrus essential oil. Subsequently, this impregnated side was knife coated with the same viscous coating solution described hereinabove and laminated with the uncoated side of another identically impregnated blotter to form a sandwich structure. The finished product was then cut into desired shape and size for use in determining the controlled release of the said citrus essential oil.

The articles so formed exhibited a uniform and prolonged release of the citrus essential oil as evidenced by a $t_{50}$, time to reach 50% release, of 19 days and a total effective release period in excess of two months.

Control samples were prepared in the same manner as described in the preceding paragraphs except that the surface coatings using the identified polymer blend were omitted. The release of citrus essential oil from these articles was fast and uncontrolled with a $t_{50}$ of only 2 days and a total effective release period of only 3 weeks.

EXAMPLE 16

This example illustrates a further advantage of the instant system in terms of reducing fractionation effects.

Initially, eight duplicate membrane laminated articles of identical dimension were prepared in the same manner as in Example 15 except that about 0.1 lb/ft$^2$ citrus essential oil and a 5 mil wet laydown coating thickness was utilized with release from these articles being followed gravimetrically. Periodically, one article was removed from the test and the residual citrus oil extracted in methylene chloride overnight. The composition of the extract was determined by Gas-Liquid Chromatography (GLC). Comparable analyses were conducted on control articles without membrane coating prepared in the same manner as in Example 15. The citrus essential oil components were categorized as high volatility (0–15 minute retention time), medium volatility (16–22 minute retention time) and low volatility (23–31 minute retention time). The cumulative release and fractionation characteristics are presented in FIGS. 1 and 2.

Figure 2:
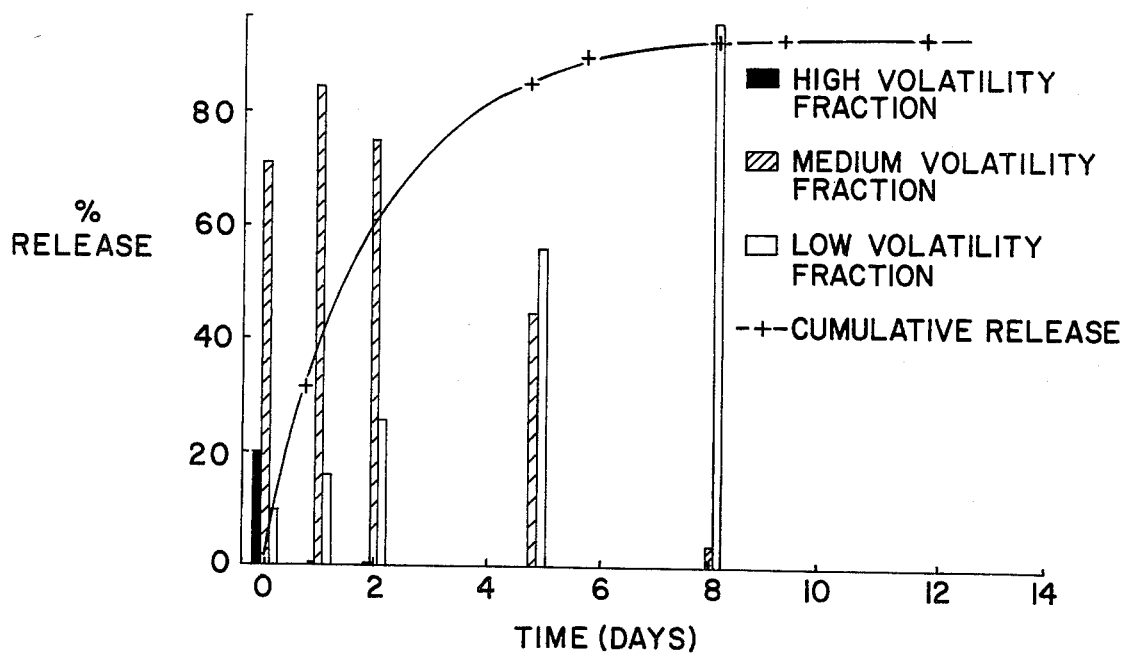

More specifically, FIG. 1 is a graphic depiction of the release of the essential oil, both cumulatively and in terms of its residual fractions, with the passage of time through the membrane laminated article, while FIG. 2 is a similar graphic depiction of release versus time from an uncoated blotter.

The graphs described hereinabove thus clearly reveal the substantial reduction in essential oil fractionation and the uniform and prolonged release of active agent from the instant systems as compared to that of the uncoated control wherein fast, uncontrolled release and undesirable essential oil fractionation prevail.

EXAMPLE 17

This example illustrates the adhesive nature of the polymer system of the instant invention and the unique advantage of said system in serving as a combined adhesive and rate controlling membrane.

A coating solution prepared in the same manner as in Example 4 was cast in a 7 mil wet laydown, using a knife coater, onto the surface of a 3 mil business grade paper (Hyolite Sub 40 manufactured by Hammermill Paper Co.) to form a paper supported membrane. The coated sheet was partially dried in a hot air oven at 80° C. whereupon said membrane coated sheet exhibiting slight tack was laminated to the blotter paper stock previously used in Example 15. About 0.08 lb/ft$^2$ of herbal essential oil was then impregnated into said absorbent blotter from the unlaminated blotter side. Subsequently, this blotter side was coated with the same viscous coating solution described hereinabove and laminated with the uncoated side of another identical impregnated blotter to form a sandwich structure. The finished product was then cut into desired shape and size for use in determining the controlled release of said herbal essential oil. The articles so formed exhibited a uniform and prolonged release of herbal essential oil for a period of over two months.

EXAMPLE 18

This example illustrates the heat activated adhesive property of the polymer system of the instant invention.

Example 17 was repeated except that the paper supported membrane was completely dried and laminated to the absorbent blotter using a heated roller. The article so formed exhibited a uniform and prolonged release of herbal essential oil for a period of over two months.

EXAMPLE 19

This example illustrates the moisture activated adhesive property of the instant polymer system.

Example 17 was again repeated except that the paper supported membrane was completely dried and laminated to the absorbent blotter after wetting the coated surface. The articles so formed also exhibited a uniform and prolonged release of herbal essential oil for a period of over two months.

EXAMPLE 20

This example demonstrates the thermal transfer of the polymer system of the present invention to a non-woven substrate.

A coating solution was prepared in the same manner as in Example 15, except that nonylphenoxy polyethoxy ethanol having 9–10 ethylene oxide units, an HLB value of 13.4 and an average molecular weight of 642 was substituted for the octylphenoxy polyethoxy ethanol. The resulting solution had a solids content of 33.3% and a Brookfield viscosity of 10,000 cps at 25° C.

The solution so formed was knife coated onto the surface of a silicone release liner with a 10 mil wet laydown. After drying in a hot air oven at 80° C., the membrane was transferred from the silicone release liner to the surface of a thin non-woven material (Reemay, style 2111, manufactured by DuPont) by being passed through heated squeeze rollers. This procedure yielded a non-woven, supported, release rate controlling membrane suitable for subsequent lamination to an appropriate substrate to provide prolonged and controlled release of volatile active agent.

EXAMPLE 21

This example illustrates the heat sealability of the polymer system of the present invention and its versatility in device construction.

A coating solution prepared in the same manner as in Example 15 was knife coated with a 5 mil wet laydown onto the surface of a 3 mil business grade paper (Hyolite Sub 40 manufactured by Hammermill Paper Co.) to form a paper supported membrane. The paper supported membrane was completely dried in a hot air oven at 80° C. and then formed into an open pouch by heat sealing three sides. An absorbent felt was inserted through the opening and 0.08 lb/ft$^2$ of citrus essential oil was impregnated into the felt. The pouch was subsequently heat sealed on the fourth side. The article so formed exhibited a uniform and prolonged release of citrus essential oil with a $t_{50}$ of 40 days and a total effective release period of three months.

EXAMPLE 22

This example illustrates another manner of forming controlled release articles using the polymer system of the present invention.

One gram of citrus essential oil was first solubilized in 2 grams of nonylphenoxy polyethoxy ethanol having 15 ethylene oxide units, an HLB value of 15.0 and an average molecular weight of 880. Thereafter, the mixture was blended with 2 grams of powdered polyacrylic acid (average M.W. 250,000) in the absence of any solvent to form a plastic dough. Subsequently, it was compressed to form a flat sheet of area 20.97 cm$^2$ and thickness of 0.2 cm.

The articles so formed exhibited a uniform and prolonged release of citrus essential oil for a period of over two months.

EXAMPLE 23

This example illustrates the controled release of medicament in articles prepared from the polymer system of the present invention.

Thus, Example 17 was repeated except that eucalyptol, an inhalational expectorant, was used as the active agent instead of herbal essential oil. The articles so formed exhibited a uniform and prolonged release of eucalyptol for a period in excess of two months.

Control samples were prepared in the same manner except that the paper supported membrane was absent. The release of eucalyptol from these samples was fast and uncontrolled.

Figure 3:
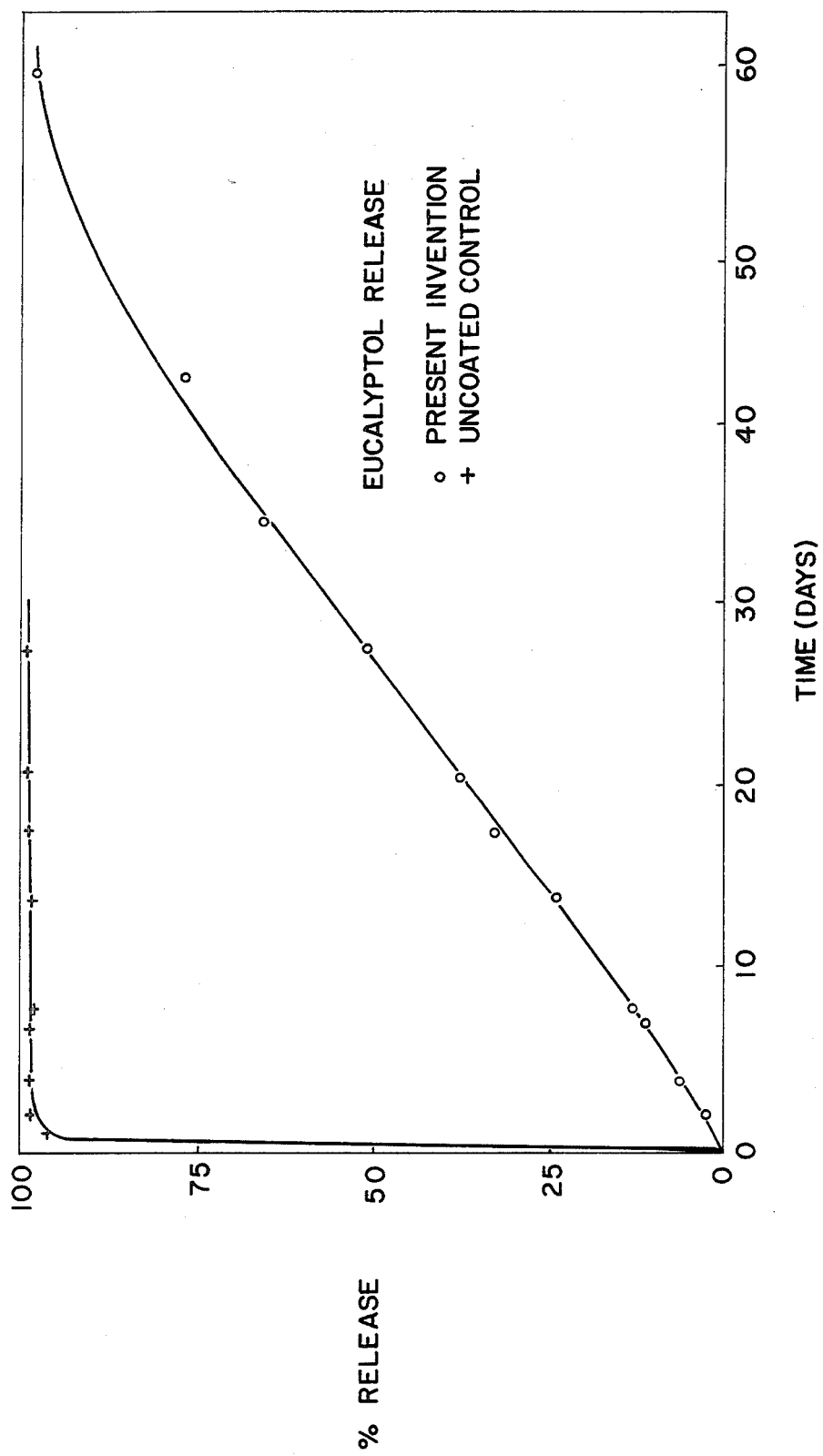

This pattern of release is depicted in FIG. 3. Thus, FIG. 3 is a graphic illustration of the % release of eucalyptol with the passage of time through the membrane laminated article as well as through an uncoated blotter.

EXAMPLE 24

This example illustrates the controlled release of pheromones in articles prepared from the polymer system of the present invention.

25 parts of a nonionic surfactant based on ethoxylated polydimethylsiloxane having 16-20 ethylene oxide units and an average molecular weight of 1,200 was blended with 167 parts of a 15% ethanol solution of polyacrylic acid having an average molecular weight of 250,000 to form a viscous solution.

The procedure of Example 17 was then repeated using the above coating solution except that 5% Grandlure, (from CHEMSAMPCO, Inc.) a boll weevil sex attractant, in mineral oil was used as the active agent instead of herbal essential oil. The articles so formed exhibited a uniform and prolonged release of Grandlure for a period of over two months.

EXAMPLE 25

This example illustrates the extrudable nature of the polymer system of the present invention.

4 parts of Carbopol 934 resin, (B. F. Goodrich), polyacrylic acid of molecular weight about 200,000 to 300,000 highly crosslinked with about 1% of polyallyl sucrose, was blended with 10 parts of Tween 80 and 5 parts of isopropanol to form a highly plastic paste. The plastic paste so formed was extruded at room temperature to form cylindrical rod shaped articles.

EXAMPLE 26

This example illustrates the utilization of the instant polymers in forming oil and water repellent film coatings.

0.5 parts of Lodyne T-21, an ethoxylated perfluoroalkyl polyurethane surfactant manufactured by CIBA-GEIGY Corporation was blended with 10 parts of 5% aqueous solution of polyacrylic acid having an average molecular weight of 250,000. Immediate precipitation was observed. Two parts of ethanol were subsequently added to the precipitate to prepare a viscous solution. The solution so formed was dip-coated on a glass slide. After air drying at room temperature, the coating showed both water and oil repellency.

EXAMPLE 27

This example illustrates the utility of the polymer system of the present invention as matrix material for the controlled release of pharmaceuticals.

About 250 parts of oxprenolol-hydrochloride, a $\beta$-blocker, was thoroughly mixed with 125 parts of Carbopol 934 and 125 parts of Tween 80. The mixture was subsequently compressed into a tablet on a laboratory tablet press.

The in-vitro release of the active ingredient from the tablet was followed by a UV spectrophotometric method. The tablet so formed exhibited uniform and prolonged release of active ingredient as evidenced by a $t_{50}$ of 2.5 hours and an effective release period of over 8 hours.

EXAMPLE 28

Example 27 was repeated except pseudoephedrin, a broncodilator from Sigma Chemical Co., was utilized therein. The tablet so formed exhibited uniform and prolonged in-vitro release of pseudoephedrine with $t_{50}$ of 2 hours and an effective release period of over 7 hours.

EAMPLE 29

This example illustrates the utility of the present polymer system in tablet coating.

About 0.5 parts of Theophylline, a diuretic from Sigma Chemical Co., was blended with 2 parts of stearyl alcohol and then compressed into a tablet having a diameter of 0.93 cm and thickness of 0.55 cm. Another identical tablet was dip-coated with a coating solution consisting of a 1:1 weight blend of Carbopol 934 and Tween 80 having a solids content of 7% in a 1:1 ethanol/isopropanol mixture. After air drying of the coating, the coated tablet exhibited uniform and prolonged in-vitro Theophylline release with a $t_{50}$ of 24 hours as compared with a $t_{50}$ of 21 hours for the uncoated control.

EXAMPLE 30

This example illustrates the utility of the polymer systems of the present invention in preparing erodible devices for the controlled release of active agents.

Ten parts of nonionic surfactant Ethofat 60/20, an ethoxylated stearic acid having 10 ethylene oxide units and an average molecular weight of 718 (manufactured by Armak Co.) was blended with 66.6 parts of 15% ethanol solution of polyacrylic acid having an average molecular weight of 250,000 to form a viscous solution with a 26.1% solids content. Three-25 part portions of the solution were blended with 0.51, 1.33 and 4.47 parts, respectively, of the dimethylamine salt of 2,4-dichlorophenoxy acetate acid (2,4-D). These mixtures were then cast in molds to form sheets.

Figure 4:
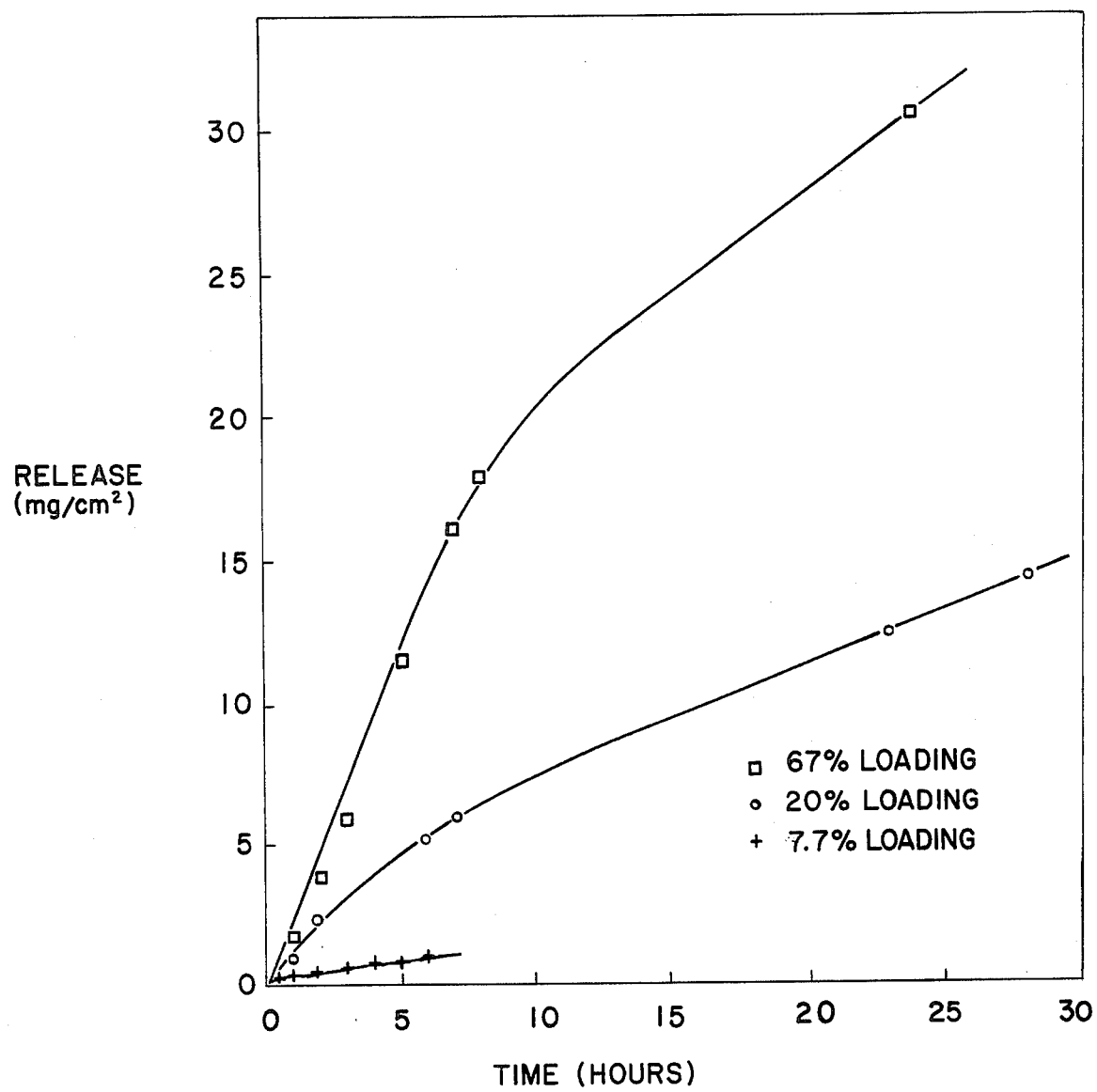

After drying under room temperature conditions, flat sheets (about 0.75 mm thick) with 7.7%, 20% and 67% of 2,4-D loading were obtained. About one square inch of each sheet was cut and adhered to an aluminum plate leaving the other surface exposed for the erosion test. The release of 2,4-D in aqueous media was measured by a UV-spectrophotometric method. The articles so formed exhibited prolonged and controlled release of 2,4-D via a polymer erosion mechanism as shown in FIG. 4. Thus, FIG. 4 is a graphic depiction of the release of 2,4-D from the erodible sheet with the passage of time, showing the percent release for three different concentrations of herbicide.

EXAMPLE 31

This example illustrates the utility of the polymer system of the present invention in the controlled delivery of systemically active pharmaceuticals to the skin or mucosa.

Thus, a 2"×2" pouch, containing 9.4 grams of Nitro-Bid ointment (2% nitroglycerine in petrolatum manufactured by Marion Laboratories), sandwiched between an impermeable aluminum foil backing and a paper supported membrane made in the same manner as in Example 17, was prepared by heat sealing along the edges with the membrane coated side facing the aluminum foil backing. The paper side of the supported membrane was then coated with a Dow Corning medical grade silicone adhesive for attaching the pouch to the target skin area.

The pouch so formed exhibited uniform and prolonged in-vitro nitroglycerine release for a period over 30 hours with a release rate around 20 $\mu g/cm^2$.hr. as measured by liquid chromatography.

EXAMPLE 32

Example 31 was repeated except that the paper supported membrane was cast from a blend of 4.76 parts of Carbopol 934, 4.76 parts of Tween 80 and 90.48 parts of 1/1 ethanol/isopropanol. The resulting dry membrane thickness (excluding the paper support) was about 0.025 mm. In addition, the Nitro-Bid ointment used in Example 31 was replaced with a 6.5% nitroglycerine-containing paste made from blending nitroglycerine on lactose (10% active) with mineral oil.

The article so prepared exhibited uniform and prolonged in-vitro nitroglycerine release for a period of over 30 hours with a release rate around 70 $\mu g/cm^2$ as measured by liquid chromatography.

EXAMPLE 33

Example 32 was repeated except the nitroglycerine containing paste was replaced with 48.49% pseudoephedrine in petroleum jelly as the reservoir.

The article so formed exhibited uniform and prolonged in-vitro pseudoephedrine release for a period of over 30 hours with a release rate around 2 $\mu g/cm^2$.hr. as measured by UV spectrophotometric method.

EXAMPLE 34

This example illustrates the utility of the present polymer system in seed coating.

Thus, about 20 grams each of corn and soybean seeds were dip coated with the solution prepared in Example 20. After draining the excess coating solution, the coated seeds were blended with bentonite to eliminate tackiness. The coated seeds were dried under room conditions and then subjected to standard germination tests.

The results of the germination tests indicated that the seed coating slightly delayed the germination time but did not affect the total percentage of seed germination.

EXAMPLE 35

This example further illustrates the use of the present polymer system in seed coating.

25 parts of a 25% aqueous solution of polyacrylic acid having an average molecular weight of 50,000 was blended with 5 parts of Triton N-101 and 3.33 parts of isopropanol to form a viscous solution having a 1 to 1 polycarboxylic acid to ethoxylated surfactant ratio. 5.66 parts of the above solution were then mixed with 20 parts of a 10% polyvinyl alcohol aqueous solution (prepared from Elvanol 71-30 resin manufactured by DuPont) to form a stable blend having a solids content of 15.6%.

The blend so formed was used to coat about 4 grams each of corn and soybean seeds according to the procedures described in Example 34. After air drying, a clear and elastic coating was observed.

EXAMPLE 36

This example demonstrates the adhesive properties of the present polymer system.

Thus, the polymer solutions described in Examples 20 and 29 were cast onto a first aluminum sheet which was laminated onto a second aluminum sheet. The samples were dried at 50° C. for five days and conditioned at room temperature and humidity for 24 hours, whereupon they were subjected to the T-peel test as described in the ASTM adhesion test method D1876-72. The results are listed below.

| Sample Source | Avg. Thickness (in.) | T-Peel Strength (lb/in width) |
| --- | --- | --- |
| Example 20 | 0.0016 | 2.49 |
| Example 29 | 0.0008 | 1.15 |

EXAMPLE 37

This example illustrates the preparative versatility of the polymer systems of the present invention.

Thus, the polymer solutions described in Examples 20 and 29 hereinabove were blended together to form a 1 to 1 mixture. Upon drying overnight at room temperature conditions, a good elastic, clear film product was obtained.

EXAMPLE 38

This example further illustrates the unexpected properties of the instant polymeric systems, particularly in comparison to the systems typical of Smith et al (U.S. Pat. No. 3,387,061).

A polymer representative of Smith et al except for the low molecular weight of the polymeric ether compound was prepared whereby 25 parts of poly(ethylene glycol) having about 10 ethylene oxide units and an average molecular weight of 400 were blended with 125 parts of 20%, by weight, aqueous solution of polyacrylic acid having an average molecular weight of 250,000. As noted by Smith, the blend was devoid of precipitation. A similar result was observed when poly(ethylene glycol) having about 5 ethylene oxide units and an average molecular weight of 200 was utilized in the blend. These solutions were then air dried at room temperature. The resulting solids exhibited multiple glass transitions upon being measured by differential scanning calorimetry, indicating a mixture morphology.

In contrast, an immediate increase in viscosity followed by precipitation was observed when a system of the instant invention was prepared utilizing 25 parts of nonylphenoxy polyethoxy ethanol having about 5 ethylene oxide units, an HLB value of 10 and an average molecular weight of 400 blended with 125 parts of 20%, by weight, aqueous solution of polyacrylic acid having an average molecular weight of 250,000. Comparable results were achieved when the nonionic surfactant was nonyphenoxy polyethoxy ethanol having 9–10 ethylene oxide units, an HLB value of 13.4 and an average molecular weight of 642. After air drying at room temperature, the resulting precipitates exhibited single glass transition values as determined by differential scanning calorimetry, similar to the pattern exhibited by homopolymers. The benefits derived from the presence of the nonionic surfactant of the instant invention are thus apparent.

EXAMPLE 39

This example further illustrates the distinction in utility between the general systems described in Example 38.

27.5 parts of nonylphenoxy polyethoxy ethanol having 9–10 ethylene oxide units, an HLB value of 13.4 and an average molecular weight of 642 were blended with 100 parts of 27.5%, by weight, aqueous solution of polyacrylic acid having an average molecular weight of 250,000, 37.2 parts of deionized water and 8.6 parts of isopropanol to form a solution with a solids content of 31.7% and a Brookfield viscosity of 8,000 cp at 25° C.

The resulting solution was knife coated with an 11 mil wet laydown onto the surface of a 3 mil business grade paper (Hyolite Sub 40 manufactured by Hammermill Paper Co.) to form a paper supported membrane. After drying in a hot air oven at 80° C., the paper supported membrane was formed into a sealed pouch containing citrus essential oil in the same manner as described in Example 21. A second sealed pouch was also prepared based on a similar paper supported membrane except that the coating solution utilized nonylphenoxy polyethoxy ethanol having about 5 ethylene oxide units, an HLB value of 10 and an average molecular weight of 440 as the surfactant component (as Example 38). These sealed pouches exhibited uniform and prolonged releases of citrus essential oil with an average $T_{50}$ of 10 days and an average total effective release period of over two months.

In contrast, when the above mentioned process was repeated utilizing low molecular weight poly(ethylene glycol) of either 5 or 10 ethylene oxide units in place of the nonylphenoxy polyethoxy ethanol, the resulting sealed pouch exhibited an almost negligible release (less than 5%) of citrus essential oil over a period of two months.

It can therefore be seen from Examples 38 and 39 that the instant systems containing the prescribed nonionic surfactants are quite distinct from systems containing a low molecular weight equivalent of the Smith et al polymeric ether compounds in flexibility of use and particularly in the ability to provide prolonged and controlled release of volatile active ingredients.

Summarizing, it is seen that this invention provides unique polymeric systems capable of a wide range of applications. Variations may be made in procedures, proportions and materials without departing from the scope of the claims.

What is claimed is:

1. Seed coated with a polymeric system comprising an association product of a polymeric carboxylic acid having free carboxyl groups on at least 10% of the monomer units thereof and an ethoxylated nonionic surfactant having at least 2 ethylene oxide units, a maximum molecular weight of 4,000 and a HLB (hydrophile-lipophile balance) value of 2 to 40.

2. The coated seed of claim 1, wherein said acid and said surfactant are present in a weight ratio of from 1:20 to 20:1.

3. The coated seed of claim 1, wherein said acid is selected from the group consisting of homopolymers of unsaturated carboxylic acids; copolymers of acrylic or methacrylic acid with at least one polymerizable vinyl compound; copolymers of acrylic or methacrylic acid with at least one polymerizable vinylidene compound; hydrolyzed interpolymers of alpha, beta-ethylenically unsaturated dicarboxylic acid anhydrides with terminally unsaturated mono-olefins, cyclic terpenes, vinyl compounds, vinylidene compounds, acrylic acid and esters thereof and methacrylic acid and esters thereof; the carboxyalkylated derivatives of polyhydroxy polymers; hydrolyzed polymers containing acrylamide or acrylonitrile groups; polycarboxylic acid ethers based on pentanoic acid residues; carboxy polymethylene hydrocolloid; and the partial esters and amides of said acids.

4. The coated seed of claim 3, wherein said acid is selected from the group consisting of polyacrylic acid, polyacrylic acid crosslinked with approximately 1% of polyallyl sucrose, polymethacrylic acid, polymaleic acid, polyitaconic acid, polyhydroxybenzoic acid, polygalacturonic acid, polyglutamic acid, polyglycollic acid, polylactic acid, ethylene/acrylic acid copolymer, ethylene/methacrylic acid copolymer, methylmethacrylate/methacrylic acid copolymer, methyl acrylate/methyl methacrylate/methacrylic acid terpolymer, ethyl acrylate/t-butyl acrylamid/acrylic acid terpolymer, methyl vinyl ether/maleic acid copolymer, vinyl acetate/crotonic acid copolymer, butadiene/maleic acid copolymer, polymaleic anhydride, acrylonitrile/maleic anhydride copolymer, butadiene/maleic anhydride copolymer, ethylene/maleic anhydride copolymer, 1-hexene/maleic anhydride copolymer, 1-octadecene/maleic anhydride copolymer, methyl vinyl ether/maleic anyhydride copolymer n-octadecyl vinyl ether/maleic anhydride copolymer, styrene/maleic anhydride copolymer, vinyl acetate/maleic anhydride copolymer, cellulose acetate phthalate, carboxymethyl cellulose, and carboxyl modified polyacrylamide.

5. The coated seed of claim 4, wherein said acid is polyacrylic acid, an ethylene-maleic acid copolymer, styrenemaleic anhydride copolymer, 1-hexene-maleic anhydride copolymer, ethylacrylate-t-butyl acrylamide-acrylic acid terpolymer polymethacrylic acid or cellulose acetate phthalate.

6. The coated seed of claim 1, wherein said ethoxylated nonionic surfactant is selected from the group consisting of ethoxylated alkylphenols, ethoxylated mono- and polyhydroxy aliphatic alcohols, ethoxylated fatty amines, ethoxylated fatty acid amides, ethoxylated fatty acid ethanolamides, ethoxylated fatty acids, ethoxylated fatty acid esters, ethoxylated sorbitan fatty acid esters, ethoxylated sorbitol esters, ethoxylated vegetable oils, ethoxylated lanolin derivatives, ethoxylated sugar derivatives, ethoxylated naphthalene derivatives, ethoxylated mercaptans, ethoxylated polypropylene glycols, ethoxylated fatty glycerides, ethoxylated fatty glycol esters and ethoxylated sucroglycerides.

7. The coated seed of claim 6, wherein said ethoxylated nonionic surfactant is selected from the group consisting of octylphenoxy polyethoxy ethanols, nonylphenoxy polyethoxy ethanols, exthoxylated sorbitan monolaurates, ethoxylated sorbitan monopalmitates, ethoxylated sorbitan monostearates, ethoxylated sorbitan monooleates, ethoxylated sorbitan tristearates, ethoxylated sorbitan trioleates, ethoxylated oleyl amides, ethoxylated tallow amides, ethoxylated glycol- laurates, ethoxylated glycol stearates, ethoxylated glycol oleates, ethoxylated stearic acid, ethoxylated oleic acid, ethoxylated rosin fatty acids, ethoxylated lauryl ethers, ethoxylated cetyl ethers, ethoxylated stearyl ethers, ethoxylated oleyl ethers, ethoxylated tridecyl ethers, ethoxylated polydimethylsiloxanes, ethoxylated polypropylene glycols, ethoxylated polyurethanes, and ethoxylated perfluoroalkyl polyurethanes.

8. The coated seed of claim 1, wherein said polymeric carboxylic acid in polyacrylic acid and said ethoxylated nonionic surfactant is nonylphenoxy polyethoxy ethanol having 9–10 ethylene oxide units, an HLB value of 13.4 and an average molecular weight of 642.

9. The coated seed of claim 1, wherein said coating also contains an active ingredient therein, said active ingredient being released at a controlled and uniform rate.

* * * * *